United States Patent [19]

Rubinstein et al.

[11] Patent Number: 5,093,113

[45] Date of Patent: Mar. 3, 1992

[54] MULTI-PHASE PERMANENT WAVING COMPOSITION

[75] Inventors: Arnold Rubinstein, Norwalk; Lynn J. Donnelly, Stamford; Ronald F. Verdi, Norwalk, all of Conn.

[73] Assignee: Shiseido Co., Ltd., Tokyo, Japan

[21] Appl. No.: 476,308

[22] Filed: Feb. 7, 1990

[51] Int. Cl.$^5$ .......................... A61L 7/09; A45D 7/04
[52] U.S. Cl. .................................... 424/72; 132/203; 514/938; 514/975
[58] Field of Search .................... 424/71, 72; 132/203, 132/204; 514/937, 938, 940, 941, 975

[56] References Cited

U.S. PATENT DOCUMENTS

| | | | |
|---|---|---|---|
| 2,479,382 | 8/1949 | Mace | 424/72 |
| 2,688,972 | 9/1954 | Brown | 424/72 X |
| 2,708,940 | 5/1955 | De Mytt et al. | 424/72 X |
| 4,301,820 | 11/1981 | Cannell et al. | 424/72 X |

FOREIGN PATENT DOCUMENTS 3009763  9/1981  Fed. Rep. of Germany.
8801860  3/1988  PCT Int'l Appl..

Primary Examiner—Thurman K. Page
Assistant Examiner—Susan S. Rucker
Attorney, Agent, or Firm—Melvin I. Stoltz

[57] ABSTRACT

A permanent wave and conditioning composition is attained by providing a first component consisting of an aesthetically pleasing, visually distinctive, dual-phase composition incorporating, in one layer thereof, hair and product enhancing agents such as hair conditioners, fragrances, and coloring agents, and a second component comprising the hair waving composition and emulsifiers. The emulsifiers assure complete dispersion and intermixing of the dual layers of the first component when the first and second components are combined. In addition, the dual-phase composition is formulated to assure separate and distinct layers are maintained for extended time periods, as well as being quickly separated when shaken.

12 Claims, No Drawings

MULTI-PHASE PERMANENT WAVING COMPOSITION

TECHNICAL FIELD

This invention relates to permanent waving compositions and, more particularly, to permanent waving compositions formulated to have at least two separate, visually distinctive immiscible components.

BACKGROUND ART

In view of the unique composition of hair fibers and the various changes in styles and fashion, the waving of hair has long been of particular interest. In order to best understand the various methods in which hair fibers can be styled or waved, it is important to remember that normal hair has three major bonds that hold the configuration of the hair and are responsible for the strength of the hair. These three bonds are salt linkages, hydrogen bonds, and disulfide bonds.

As is well known, hair is a protein produced from units known as "amino acids". A high proportion of these are diamino and dicarboxylic "amino acids", and thus the hair fiber is amphoteric in character. Since the number of free acid and basic groups are approximately equal, the hair's mechanical properties, such as its strength, is at its maximum at neutrality (pH 7). For example, the fiber becomes easier to stretch as the pH increases or decreases from pH 7. The cohesion of hair is also demonstrated by the minimum swelling in water at neutrality.

Because they are so numerous, the hydrogen bonds, involving the amino hydrogen and carbonyl oxygen of the amide linkages, are most important. Water, particularly in the monomolecular state, as occurs with moisture in the air (humidity), can weaken these bonds, by becoming a part of a hydrogen bonding structure. However, some of these hydrogen bonds are protected by hydrophobic bonds and will remain even when the hair is wet with water. More powerful hydrogen bond breakers, like high concentration of lithium bromide and urea are required for complete breakage of all hydrogen bonds.

As long as the hair fiber is dry, the strength of the hair fiber is not reduced. For example, a straight hair, wet with water and held by mechanical force in a curly configuration while drying will remain in a curly shape due to the formed hydrogen bonds and salt linkages, and it will not return to its straight shape so long as it remains dry. However, unless mechanically restrained, upon being wet with water, the hair will lose its curly configuration and become straight.

Furthermore, when hair is set by the use of water alone, the hair will gradually lose its curly shape through the absorption of atmospheric moisture and the resulting rearrangement of the hydrogen bonds. This is due to the fact that in water, the dominant bond is disulfide bond, while in the dry state, the dominant bonds are the salt linkages and the hydrogen bonds.

In regard to the disulfide bonds, hair is composed of a unique protein material called "keratin", which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links adjacent polypeptide chains (K) through two sulfur atoms (S-S) to give keratin protein (K-S-S-K). Only by chemical action can this covalent linkage be broken.

Similarly, it is well established that in order to permanently wave hair, this disulfide linkage must be broken. In this regard, many prior art compositions have been developed for the "cold permanent waving" of hair. Typically, these prior art systems treat the hair with a reducing agent which breaks the disulfide (cystine) linkage in the hair while the hair is wound around a curling rod. These prior art systems are typified by the disclosures in U.S. Pat. Nos. 2,479,382, 2,577,710, 2,577,711, 2,688,972, and 2,708,940.

It is believed that certain hydrogen bonds are protected by the cystine bond and are only broken by water when the cystine bond is split into two cysteine moieties. By the same rationale, these hydrogen bonds are re-formed in the new configuration and protected by the newly formed cystine bonds created in the neutralization step of permanent waving. In effect, these protected hydrogen bonds supplement the disulfide bonds in creating permanency to the new curl configuration.

In general, permanent hair waving is usually carried out by subjecting the hair to reagents containing a free—SH group or thiol. These materials are also called mercaptans. In this treatment, the hair is usually first wound on rollers and then saturated with thiol. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equation:

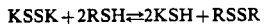

$$KSSK + 2RSH \rightleftharpoons 2KSH + RSSR$$

When a sufficient number of hair disulfide bonds have been broken, the hair is realigned to pair previously unpaired hair protein thiol groups opposite each other. At this point, the hair is rinsed, removing the unreacted thiol waving agent and disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

The rebonding of the reduced sites accomplished by the action of the chemical oxidizing agent is illustrated by the following chemical reaction:

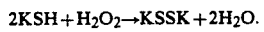

$$2KSH + H_2O_2 \rightarrow KSSK + 2H_2O.$$

Presently, two types of permanent wave compositions are most often employed to saturate the hair with the requisite thiol waving agent. One such composition is based upon the use of ammonium thioglycolate while the other conventional composition employs glyceryl monothioglycolate (GMT). The principal differences between these two hair waving compositions is the pH at which these compositions operate, with the GMT composition being capable of providing the desired permanent wave to the hair at a lower pH, usually ranging between 6.5 and 8.

In addition to the thiol waving agent, these hair waving compositions typically incorporate hair enhancing additives, such as conditioning agents and fragrances to provide added luster and sheen to the hair, as well as a pleasing aroma. In the hair waving compositions employing the ammonium thiolgylcolate, these additives are usually mixed directly with the ammonium thiolgylcolate to form a single, permanent waving composition.

However, in the permanent waving compositions employing GMT, hair enhancing additives are typically mixed with the GMT immediately prior to application of the composition to the hair. As a result, any hair enhancing additives to be employed with the permanent wave composition must be packaged and distributed separately from the GMT-based permanent wave composition.

This requirement for separate packaging is due to the propensity GMT has to react or break down when mixed with other components for long periods of time. Consequently, hair waving compositions employing GMT as the thiol waving agent require two independent, separate containers, one container for the GMT hair waving composition and a second container for the hair enhancing additives.

Although GMT based permanent waved compositions have been widely sold and distributed, the requirement that these permanent waving composition be distributed in two separate and distinct containers has led to various packaging and distribution problems inherent in creating and distributing a two-container product which is both functional and visually pleasing. Alternatively, these prior art products have been sold as a single component product with the more desirable conditioning and fragrance additives being sacrificed.

Therefore, it is a principal object of the present invention to provide a permanent waving composition which is formulated for optimum hair waving and conditioning, while also providing a unique, visually distinctive appearance.

Another object of the present invention is to provide a permanent wave composition having the characteristic features defined above which is formulated to provide a plurality of separate and distinct phases or layers which remain immiscible throughout the distribution process and are homogeneously mixable upon use.

Another object of the present invention is to provide a permanent wave composition having the characteristic features described above which provides the enhanced, visually distinctive multi-phases, without in any way compromising the efficacy of the permanent wave composition.

Another object of the present invention is to provide a permanent wave composition having the characteristic features described above which provides a multiphase composition for one of the components of a GMT based permanent waved composition.

Other and more specific objects will in part be obvious and will in part appear hereinafter.

DETAILED DESCRIPTION

The present invention overcomes the prior art drawbacks and difficulties by providing a unique permanent wave composition incorporating effective hair enhancing additives formulated to provide at least two immiscible phases. In this way, a unique, distinctive, and aesthetically pleasing appearance is achieved, in combination with an effective permanent waving and conditioning product. Although the present invention is applicable to all permanent wave compositions, the following disclosure details the preferred embodiment of the present invention as formulated for an acid balanced or permanent wave composition employing glyceryl monothiolglycolate (GMT) as the principal permanent waving constituent.

As previously discussed, it has been found that GMT is unable to retain its efficacy as a permanent waving component when the GMT is mixed and stored with other additives for long time periods. As a result, permanent wave compositions employing GMT and hair enhancing additives must be formulated for distribution and sale in two separate and distinct packages or containers. The contents of the two containers are mixed together immediately prior to their use.

In order to provide added hair enhancement during the permanent waving process, as well as impart a unique, visually distinctive and aesthetically pleasing dual-phase GMT based permanent wave composition, a unique formulation has been developed. By employing the present invention, a GMT based or acid balance permanent wave composition is attained which not only provides an effective, long-lasting permanent wave with optimum hair conditioning and desirable fragrance, but also attains a permanent wave composition which is visually unique and aesthetically pleasing.

The acid balanced permanent waving composition of the present invention comprises two separate and distinct components which are retained in independent containers. One container incorporates the GMT formulation, while the second container houses the visually distinctive and aesthetically pleasing dual-phase formulation incorporating the hair enhancing additives. Both formulations are retained in separate containers during transportation and storage, and are intermixed immediately prior to their application to the hair.

The dual phase formulation of this invention preferably comprises liquid water as one phase and a water immiscible layer as the second phase. Preferably, the water immiscible layer incorporates the hair and product enhancing additives, such as conditioning agents, fragrances, and color additives to further enhance the visual characteristics of this phase of the formulation.

In order for the dual phase formulation to possess and maintain the desired appearance prior to use, the layers must separate quickly when shaken or otherwise mixed, and the water immiscible phase must have a specific gravity less than 1.000. In addition, the hair conditioning agents incorporated into the water immiscible phase must be present in sufficient quantity to provide the desired sheen, luster and hair manageability needed for an effective and desirable permanent wave composition, while not leaving the hair feeling greasy or coated. Furthermore, the hair enhancing additives should not interfere, in any way, with the permanent waving process or cause early curl relaxation to occur.

In the preferred embodiment, the conditioning agent employed in the water immiscible layer of the dual phase formulation of the present invention comprises petroleum fraction which distills between 225° and 500° F. In particular, highly saturated, isoparaffinic, petroleum based compositions have been found to provide the most desirable constituent for use in the water immiscible layer.

Preferably, the highly saturated isoparaffinic petroleum based composition for use in this invention comprises one or more selected from the family of compounds known by the trade name "ISOPAR", distributed by Exxon Company U.S.A. of Houston, Tex. It has been found that for use in the present invention, the preferred Isopar or Isopar blends are selected from the group of compounds which distill between 240° F. and 270° F. and comprise 99% saturated hydrocarbons. The preferred compound has the trade name ISOPAR E, and is also known by its CTFA designation as C8-9 Isoparafin.

In addition to the Isopar or Isopar blend incorporated into the water immiscible layer, the formulation of the water immiscible layer also incorporates a desired quantity of fragrance, and a coloring additive to impart to the water immiscible layer a visually distinctive and aesthetically pleasing appearance.

The second phase of the dual phase formulation is preferably formed substantially entirely by water. In order to assure the proper separation and non-contaminated nature desired for the product, deionized water is preferred. In addition, between about 1% and 5% of the second phase also comprises 28% ammonium hydroxide in order to further enhance the overall stability of the dual phase formulation.

It has been found that the dual phase formulation detailed above provides the desired visually distinctive and aesthetically pleasing composition for this component of the permanent wave product. In addition, due to the unique formulation attained by the present invention, the two phases are fast separating, so that any shaking or movement during transportation or prior to actual use does not cause any unwanted intermixing of the dual composition.

In order to provide long lasting, effective permanent waving of the hair with optimum manageability and fragrance, the GMT formulation is constructed to be completely intermixable with the dual phase formulation to achieve a single, homogeneous composition for application to the hair. Furthermore, once intermixed, a stable homogeneous permanent wave composition is attained which is usable throughout the permanent wave treatment process. Preferably, glycerin is also employed in the GMT formulation as a modifier therefor.

In order to attain the desired homogeneous intermixing of the GMT formulation and the dual phase formulation, an emulsifying agent is employed. In the preferred embodiment, the emulsifying agent is incorporated into the GMT formulation. However, in addition to providing the desired mixing of the dual phase formulation, the emulsifying agent is chemically inert when mixed with only the GMT. In this way, the permanent waving capabilities of the GMT are fully retained and discoloration or product degradation does not occur.

The principal emulsifying agents which possess the required attributes are based upon natural almond oil, palm kernel oil, or corn oil. It has been found that to attain the desired attributes, these agents must be condensed with ethylene oxide to form materials containing 20% to 60% ethylene oxide. The resulting emulsifiers can be used individually, or in blends, or in combinations depending upon the particular end use being sought. However, regardless of the particular formulation employed, it has been found that the emulsifying agents preferably range between about 2.5% and 10% by weight of the entire composition.

In the preferred embodiment, the emulsifying agents comprise a blend of PEG-12 palm kernel glyceride and PEG-45 palm kernel glyceride. These designations are the CTFA designations for these products. However, it has been found that Crovol PK-40 and Crovol PK-70 comprise the preferred constituents. These designations are trade names of Croda, Inc., 183 Madison Avenue, New York, N.Y. 10016.

It has also been found that the preferred emulsifying agents possess, either individually or in their blended formulations, a saponification value ranging from about 40 to 140 and a hydroxyl value ranging between about 60 and 175. Although various blends or individual emulsifying agents meeting the criteria detailed above can be attained, these physical characteristics have been found to provide the preferred ranges for the preferred emulsification additives.

In Table 1, the preferred formulation for the permanent wave and conditioning composition of the present invention is provided. As detailed therein, the preferred embodiment comprises an exothermic reaction upon mixing, since it has been found that an exothermic reaction increases wave or curl retention. However, if an exothermic reaction is not desired, additional water can be substituted for the sodium bromate in Part B-lower layer.

TABLE 1

| Part A | Range % By Weight | Preferred % By Weight |
|---|---|---|
| Glycerylmonothioglycolate | 80-90 | 86.1 |
| Glycerin | 5-10 | 7.3 |
| PEG-45 Palm Kernel Glyceride | 1.5-6.5 | 4.5 |
| PEG-12 Palm Kernel Glyceride | 1-3.5 | 2.1 |

| Part B | Range % By Volume | Preferred % By Volume |
|---|---|---|
| Upper Layer | | |
| C-8 Isoparafin | | 84 |
| Fragrance | | 15 |
| Color | | trace |
| Silicon | | 1 |
| Lower Layer | | |
| Deionized Water | 93.9-98.1 | 96.6 |
| Amm. Hydroxide (28%) | 1-5 | 2.4 |
| Sodium Bromate | .9-1.1 | 1.0 |

Mix 70 grams (plus or minus 1 gram) of Part B-lower with 3.2 grams (plus or minus 0.3 grams) of Part B-upper
To attain the final composition for application to the hair, mix 29.7 milliliters of Part A with 74 milliliters of Part B.

As detailed above, the upper, immiscible layer of the dual phase component preferably comprises about 4.4% by weight of the entire dual phase component. However, it has been found that a highly effective, aesthetically pleasing dual phase component is attained with the upper, immiscible layer ranging between about 4% and 5% of the dual phase component.

EXAMPLES

In order to prove the efficacy of the present invention, a permanent waving conditioning composition was prepared in accordance with the preferred formulation detailed in Table 1. The dual phase component (Part B) successfully established two completely independent layers, which would separate immediately after the shaking and remained separate and distinct.

Upon mixing Part A and Part B together, the immiscible layer was emulsified and thoroughly intermixed with the remaining components, providing a homogeneous intermixed composition. The permanent waving and conditioning composition was then applied to an individual having full-length tinted hair, and the conventional permanent wave procedures were followed.

The resulting permanent wave exhibited very good curl configurations throughout the entire head of hair, as well as very good wet combing characteristics. In addition, the conditioning qualities of the hair were very good.

The resulting curls were soft and springy and the wet and dry hair was easy to manage. Furthermore, the resulting hair had a nice, smooth feel with lots of luster. When the permanent wave was rechecked upon return, very good curl and condition results were observed. The curl had held up with no relaxation and the condition of the hair was very good.

Similar head tests were conducted on several other individuals, each having differing hair textures and hair types. In each additional test, the identical formulation as defined above was employed and the resulting permanent wave and conditioning effect of the hair in each instance was virtually identical, ranging between excellent and good.

It will thus be seen that the objects set forth above, among those made apparent in the preceding description, are efficiently attained and, since certain changes may be made in the above composition, without departing from the scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or components recited in the singular are intended to include compatible mixtures of such ingredients whenever the sense permits.

Having described our invention, what we claim as new and desire to secure by Letters Patent is:

1. A visually distinctive, aesthetically pleasing, and highly effective permanent wave and conditioning composition comprising
    A. a first component maintained in a first container and comprising between about 75% and 95% by weight of glycerylmonothioglycolate and between about 5% and 25% by weight of at least one emulsifying agent selected from the group consisting of ethoxylated emulsifying agents formed by condensation of the base material with ethylene oxide to form materials containing 20% to 60% ethylene oxide and emulsifying agents having a saponification value ranging between about 40 to 140 and a hydroxyl value ranging between about 65 and 175; and
    B. a duel phase second component maintained in a second container and comprising two visually distinctive separate, immiscible layers
        a. said first layer comprising water, and
        b. said second layer having a water immiscible composition with a specific gravity less than 1.000 which quickly separates from the water layer until mixed with the emulsifying agents of the first component, and comprising one or more hair/product enhancing additives selected from the group consisting of hair conditioning agents, fragrances and color additives, whereby a visually distinctive permanent waving and conditioning composition is attained wherein two visually distinctive separate layers are maintained until mixed with the first component prior to use.

2. The permanent wave and conditioning composition defined in claim 1, wherein the second layer of the second component is further defined as having a specific gravity less than 1.0.

3. The permanent wave and conditioning composition defined in claim 1, wherein the hair conditioning agent is further defined as comprising one or more highly saturated, isoparaffinic, petroleum based compositions which distill between 225° and 500° F.

4. The permanent wave and conditioning composition defined in claim 3, wherein the hair conditioning agent is further defined as comprising a single or blend of isoparaffinic petroleum based compounds which distill between 240° and 270° F. and have a 99% level of saturated hydrocarbons.

5. The permanent wave and conditioning composition defined in claim 3, wherein the first layer of the second component is further defined as comprising between about 95% and 99% deionized water and between about 1% and 5% of a 28% solution of ammonium hydroxide.

6. The permanent wave and conditioning composition defined in claim 3, wherein the emulsifying agent of the first component is further defined as being based upon one or more selected from the group consisting of almond oil, palm kernel oil, and corn oil.

7. The permanent wave and conditioning composition defined in claim 6, wherein the emulsifying agent is further defined as being condensed with ethylene oxide to form materials containing 20% to 60% ethylene oxide.

8. The permanent wave and conditioning composition defined in claim 7, wherein the emulsifying agent comprises between about 2.5% and 10% by weight of the first component, a saponification value ranging between about 40 and 140, and a hydroxyl value ranging between about 60 and 175.

9. The permanent wave and conditioning composition defined in claim 3, wherein the emulsifying agent comprises one or more selected from the group consisting of PEG-12 palm kernel glyceride and PEG-45 palm kernel glyceride.

10. A visually distinctive, aesthetically pleasing, and highly effective permanent wave and conditioning composition comprising
    A. a first component maintained in a first container and consisting essentially of
        a. between about 80% and 90% by weight glycerylmonothioglycolate, and
        b. between about 5% and 10% by weight glycerin, and
        c. between about 2.5% and 10% by weight of one or more emulsifying agents consisting of water dispersible and water soluble emollients formed by the ethoxylation of one selected from the group consisting of almond oil, palm kernel oil, and corn oil by condensation with ethylene oxide to form materials containing 20% to 60% ethylene oxide; and
    B. a duel phase second component maintained in a second container and comprising two visually distinctive separate, immiscible layers
        a. said first layer comprising
            1. between about 95% and 99% deionized water, and
            2. between about 1% and 5% of a 28% solution of ammonium hydroxide, and b. said second layer comprises a fast separating, water immiscible composition having a specific gravity less than 1.0 and comprising one or more conditioning agents selected from the group consisting of isoparaffinic petroleum based compounds which distill between 240° and 270° F. and have a 99% level of saturated hydrocarbons.

11. The permanent wave and conditioning composition defined in claim 10 wherein said second layer is further defined as comprising fragrance and color additives.

12. The permanent wave and conditioning composition defined in claim 11, wherein the second layer comprises between about 4% and 5% by weight of the second component and consists essentially of
 1. about 84% by volume C8-9 isoparafin,
 2. about 15% fragrance,
 3. about 1% silicone, and
 4. trace amounts of a coloring additive.

* * * * *